(12) United States Patent
Schiff et al.

(10) Patent No.: US 12,053,612 B1
(45) Date of Patent: Aug. 6, 2024

(54) DRUG DISPENSING SYSTEM WITH REPLACEABLE DRUG SUPPLY CARTRIDGES

(71) Applicant: Fresenius Kabi Deutschland GmbH, Bad Homburg (DE)

(72) Inventors: David R. Schiff, Highland Park, NJ (US); Sharon D. West, Elkins Park, PA (US)

(73) Assignee: Hollister Incorporated, Libertyville, IL (US)

( * ) Notice: Subject to any disclaimer, the term of this patent is extended or adjusted under 35 U.S.C. 154(b) by 105 days.

(21) Appl. No.: 17/752,438

(22) Filed: May 24, 2022

Related U.S. Application Data

(62) Division of application No. 17/246,125, filed on Apr. 30, 2021, now Pat. No. 11,351,300.

(51) Int. Cl.
*A61M 5/142* (2006.01)
*A61M 5/145* (2006.01)

(52) U.S. Cl.
CPC ........ *A61M 5/14248* (2013.01); *A61M 5/145* (2013.01); *A61M 5/1456* (2013.01); *A61M 5/14566* (2013.01); *A61M 2205/3331* (2013.01)

(58) Field of Classification Search
CPC ................ A61M 5/145; A61M 5/1456; A61M 5/14255; A61M 5/5086; A61M 2005/14268
See application file for complete search history.

(56) References Cited

U.S. PATENT DOCUMENTS

| | | | |
|---|---|---|---|
| 8,285,328 B2 * | 10/2012 | Caffey | A61M 5/14526 417/213 |
| 8,902,433 B2 * | 12/2014 | Schlaeppi | A61M 5/1456 356/614 |
| 9,452,255 B2 | 9/2016 | Tieck et al. | |
| 2003/0167036 A1 | 9/2003 | Flaherty | |
| 2004/0116866 A1 | 6/2004 | Gorman et al. | |
| 2004/0199123 A1 | 10/2004 | Nielsen | |
| 2008/0091139 A1 | 4/2008 | Srinivasan et al. | |
| 2008/0125700 A1 | 5/2008 | Moberg et al. | |
| 2009/0131860 A1 | 5/2009 | Nielsen | |
| 2010/0137832 A1 | 6/2010 | Mathews et al. | |
| 2010/0262078 A1 | 10/2010 | Blomquist | |
| 2011/0178461 A1 | 7/2011 | Chong et al. | |
| 2012/0010594 A1 | 1/2012 | Holt et al. | |
| 2015/0374919 A1 | 12/2015 | Gibson | |
| 2016/0038689 A1 | 2/2016 | Lee et al. | |
| 2016/0082182 A1 | 3/2016 | Gregory et al. | |
| 2016/0199574 A1 | 7/2016 | Ring et al. | |
| 2016/0220798 A1 | 8/2016 | Netzel et al. | |
| 2016/0296704 A1 | 10/2016 | Gibson | |
| 2016/0354555 A1 | 12/2016 | Gibson et al. | |
| 2017/0119969 A1 | 5/2017 | McCullough et al. | |
| 2017/0124284 A1 | 5/2017 | McCullough et al. | |

(Continued)

FOREIGN PATENT DOCUMENTS

| | | |
|---|---|---|
| WO | 2018081234 A1 | 5/2018 |
| WO | 2018183039 A1 | 10/2018 |

(Continued)

*Primary Examiner* — Laura A Bouchelle
(74) *Attorney, Agent, or Firm* — Cook Alex Ltd.

(57) ABSTRACT

A drug dispensing system with replaceable cartridges wherein the system indicates whether the cartridge is suitable for use.

19 Claims, 8 Drawing Sheets

(56) References Cited

U.S. PATENT DOCUMENTS

| | | |
|---|---|---|
| 2017/0147787 A1 | 5/2017 | Albrecht et al. |
| 2017/0182253 A1 | 6/2017 | Folk et al. |
| 2017/0340837 A1 | 11/2017 | Nazzaro et al. |
| 2017/0361015 A1 | 12/2017 | McCullough |
| 2017/0368260 A1 | 12/2017 | McCullough et al. |
| 2018/0021508 A1 | 1/2018 | Destefano et al. |
| 2018/0028747 A1 | 2/2018 | Hanson et al. |
| 2018/0036476 A1 | 2/2018 | McCullough et al. |
| 2018/0085517 A1 | 3/2018 | Laurence et al. |
| 2018/0256823 A1 | 9/2018 | Nazzaro et al. |
| 2018/0272059 A1 | 9/2018 | Marbet et al. |
| 2018/0304014 A1 | 10/2018 | Knudsen et al. |
| 2019/0009019 A1 | 1/2019 | Shor et al. |
| 2019/0022306 A1 | 1/2019 | Gibson et al. |
| 2019/0050375 A1 | 2/2019 | Fitzgibbon et al. |
| 2019/0060562 A1 | 2/2019 | Olivas et al. |
| 2019/0083702 A1 | 3/2019 | Nekouzadeh et al. |
| 2019/0134296 A1 | 5/2019 | Barbedette et al. |
| 2019/0143043 A1 | 5/2019 | Coles et al. |
| 2019/0143047 A1 | 5/2019 | Jazayeri et al. |
| 2019/0151544 A1 | 5/2019 | Stonecipher |
| 2019/0167908 A1 | 6/2019 | Fitzgibbon et al. |
| 2019/0192766 A1 | 6/2019 | Stonecipher |
| 2019/0247579 A1 | 8/2019 | Damestani |
| 2019/0275241 A1 | 9/2019 | Ring et al. |
| 2019/0328965 A1 | 10/2019 | Moberg |
| 2019/0365986 A1 | 12/2019 | Coiner et al. |
| 2019/0374707 A1 | 12/2019 | Damestani et al. |
| 2019/0381238 A1 | 12/2019 | Stonecipher et al. |
| 2020/0023122 A1 | 1/2020 | McCullough et al. |
| 2020/0164145 A1 | 5/2020 | Chang et al. |
| 2020/0164155 A1 | 5/2020 | Mojarrad et al. |
| 2020/0179609 A1 | 6/2020 | Tan-Malecki et al. |
| 2020/0197628 A1 | 6/2020 | McCullough et al. |
| 2020/0206429 A1 | 7/2020 | Hering et al. |
| 2020/0230313 A1 | 7/2020 | Mojarrad et al. |
| 2020/0238004 A1 | 7/2020 | McCullough |
| 2020/0254172 A1 | 8/2020 | Forster et al. |
| 2020/0261643 A1 | 8/2020 | Boyaval et al. |
| 2020/0261648 A1 | 8/2020 | Groszmann et al. |
| 2020/0261657 A1 | 8/2020 | Gibson et al. |
| 2020/0289745 A1 | 9/2020 | Harris et al. |
| 2020/0297927 A1 | 9/2020 | Conrath et al. |
| 2020/0322793 A1 | 10/2020 | Yang |
| 2020/0338271 A1 | 10/2020 | Harris et al. |

FOREIGN PATENT DOCUMENTS

| | | |
|---|---|---|
| WO | 2018226565 A1 | 12/2018 |
| WO | 2019018169 A1 | 1/2019 |
| WO | 2019022950 A1 | 1/2019 |
| WO | 2019022951 A1 | 1/2019 |
| WO | 2019032101 A1 | 2/2019 |
| WO | 2019143753 A1 | 7/2019 |

* cited by examiner

DRUG DISPENSING SYSTEM WITH REPLACEABLE DRUG SUPPLY CARTRIDGES

RELATED APPLICATIONS

This application is divisional of prior application Ser. No. 17/246,125, filed Apr. 30, 2021, which is hereby incorporated herein by reference.

FIELD OF THE DISCLOSURE

The present disclosure relates to drug delivery devices and dispensing systems. More particularly, the present disclosure relates to on-body dispensing systems adhered to the patient's body for automatically delivering a drug to the patient. Even more particularly, the present disclosure relates to dispensing systems that indicate whether a replaceable cartridge is suitable for use.

DESCRIPTION OF RELATED ART

Delivery of liquid drugs to a patient via injection using a needle or syringe is well-known. More recently, devices that automate the delivery of liquid drugs have been introduced. These devices (which are commonly referred to as "on-body devices" or "on-body injectors") are mounted or otherwise secured to the body of the patient (e.g., to the arm or abdomen) and remain in place for an extended amount of time (on the order of hours or days), injecting an amount of the drug into the body of the patient at one or more scheduled times. For example, a device may be configured to deliver a drug over the span of 45 minutes, with delivery beginning 27 hours after the device has been activated and applied to a patient (to ensure that the drug is not delivered sooner than 24 hours after a medical procedure or treatment). These devices improve upon manual methods by obviating the need for the patient to inject themselves with the drug (which carries heightened risks of the patient improperly administering the injection or injecting the drug at an inappropriate time) or to return to a medical facility for one or more injections by a technician or medical professional.

One known on-body device 10 is shown in FIGS. 1 and 2. The device 10 of FIG. 1 includes a housing 12 that contains or encloses the functional components of the device 10, which are shown in FIGS. 3 and 4.

The internal components of the device 10 include a reservoir 14 that is configured to be filled with a liquid drug to be delivered to the patient. An upper surface of the housing 12 includes a fill indicator 16 that provides a visual indication of the amount of fluid in the reservoir 14. In addition to the fill indicator 16, the upper surface of the housing 12 may include printed information, such as information regarding the drug to be delivered. The upper surface of the housing 12 may be formed of a translucent material, which allows light from a status light 18 (which may be configured as a light-emitting diode) mounted within the housing 12 (FIG. 1) to be seen through the upper surface of the housing 12. The status light 18 is electrically coupled to a controller or processor (which may be a CPU or MPU configured as a computer chip mounted to a printed circuit board positioned within the housing 12, for example) that carries software for executing a drug delivery routine. The status light 18 receives signals from the controller and emits light to provide information regarding a status of the device 10. This may include emitting differently colored light and/or emitting light in different flashing patterns to indicate different conditions, such as a blinking orange light to indicate that the device 10 is ready to be applied to a patient, a blinking green light to indicate proper operation of the device 10, and a blinking red light to indicate an error or other condition. One or more batteries 20 provides power to the status light 18 and the other electrical components of the device 10.

The drug is injected into the reservoir 14 using a (typically pre-filled) syringe 22 via a port 24 incorporated into the bottom or underside of the housing 12 (FIG. 4) and fluidly connected to the reservoir 14. FIGS. 1 and 2 illustrate an applicator 26 that is removably associated with the underside of the housing 12 and used in combination with the syringe 22 to fill the reservoir 14 via the port 24. The drug is most typically injected into the reservoir 14 by a medical professional immediately before the device 10 is secured to the patient to ensure that the proper drug is supplied, along with the proper amount.

A piston or plunger 28 (FIG. 4) positioned within the reservoir 14 is moved (from left to right, in the orientation of FIG. 4) as the space within the reservoir 14 is filled by the inflowing drug. Movement of the piston 28 into its final position (when the reservoir 14 has been filled with the appropriate amount of the drug) causes a portion of a rod associated with the piston 28 to extend from the reservoir 14 to create an electrical connection, which activates the device 10. Activation of the device 10 may include a signal, such as a buzzer providing an audible indication that the device 10 has been activated and/or a light emitted by the status light 18.

When the device 10 has been activated, it is mounted or secured to the body of the patient. The applicator 26 is first removed from the underside of the housing 12 and discarded, followed by a pull tab 30 being manipulated to remove a release film from an adhesive pad 32 associated with the underside of the housing 12. The housing 12 is then pressed against the body of the patient, with the adhesive pad 32 facing the body. An adhesive present on the adhesive pad 32 causes the adhesive pad 32 (and, hence, the housing 12) to adhere to the body.

Some predetermined time after the device 10 has been activated (which may be on the order of three to five minutes, for example), a distal end portion of a cannula 34 is introduced into the skin of the patient via a cannula window 36 defined in the housing 12 (FIGS. 3 and 4). The cannula 34 (which remains partially positioned within the skin of the patient for as long as the device 10 is in use) is formed of a flexible or semi-rigid material, such as a plastic material, for improved patient comfort.

As the cannula 34 is not itself configured to pierce the skin, an associated needle 38 is provided within the lumen of the cannula 34, with a sharp or beveled distal end of the needle 38 extending out of a distal end of the cannula 34. A midsection of the needle 38 is mounted within a needle carriage 40, while a proximal end 42 of the cannula 34 is mounted within a cannula carriage 44 that is initially positioned directly adjacent to the needle carriage 40. The needle carriage 40 is pivotally connected to an end of a linkage or crank arm 46, with an opposite end of the linkage 46 being associated with a torsion spring 48. At the designated time (e.g., 3-5 minutes after the device 10 has been activated), the controller causes a lever (not visible) to be released, which allows the spring 48 to recoil, in turn rotating the linkage 46, which rotation causes the needle carriage 40 to move along a linear track 50 from a first position adjacent to the spring 48 (FIG. 3) to a second position spaced away from the spring 48. Movement of the needle carriage 40 causes corresponding movement of the cannula carriage 44 along the track 50, with the cannula 34 and the distal portion of the needle 38 moving together in a direction away from the spring 48. Moving the carriages 40 and 44 into the second position causes the sharp distal end of the needle 38 to advance out of the housing 12 via the cannula window 36 and pierce the skin. The cannula 34 is carried by or moves along with the distal portion of the needle 38, such that the needle 38 piercing the skin will also cause the distal end of the cannula 34 to enter into the skin.

Continued recoiling of the spring 48 causes further rotation of the linkage 46, which has the effect of moving the needle carriage 40 back toward the spring 48 (i.e., back toward its first position). Rather than moving along with the needle carriage 40, the cannula carriage 44 is held in its second position (FIG. 3) by a lock or latch 52. As the movement of the needle carriage 40 is not restricted by the lock or latch 52, the needle carriage 40 will return to its first position, while the cannula carriage 44 remains in its second position (with the final positions of both carriages 40 and 44 shown in FIG. 3).

Movement of the needle carriage 40 in a proximal direction away from the cannula carriage 44 causes the needle 38 to partially (but not fully) retract from the cannula 34. In the final condition shown in FIG. 3, the distal end of the needle 38 is positioned within the cannula 34 (e.g., adjacent to a midsection or midpoint of the cannula 34), while the distal end of the cannula 34 remains positioned within the skin. A proximal end of the needle 38 extends into fluid communication with the reservoir 14, such that the needle 38 provides a fluid path from the reservoir 14 to the cannula 34 when the carriages 40 and 44 are in the final condition illustrated in FIG. 3. Due to the distal end of the cannula 34 remaining positioned within the skin, subsequent advancement of the drug out of the reservoir 14 (e.g., 27 hours after the device 10 has been activated) will cause the drug to move into the needle 38 (via the proximal end of the needle 38), through the needle 38 (to its distal end), and into the cannula 34. The drug is then delivered to the patient (e.g., over the course of a 45-minute session) via the distal end of the cannula 34 positioned within the skin.

As for the mechanism by which the drug is advanced out of the reservoir 14, the device 10 includes a lever 54 mounted to a pivot point 56 (FIG. 4). The lever 54 includes a first arm 58 configured and oriented to interact with a first gear 60 and a second arm 62 configured and oriented to interact with a second gear 64. A tab 66 extends from an opposite end of the lever 54 and is configured and oriented to alternately move into and out of contact with two electrical contacts 68 and 70 (electrically coupled to a printed circuit board, which is not shown) as the lever 54 pivots about the pivot point 56.

A first wire or filament 72 extends from the lever 54, around a first pulley 74, and into association with a first electrical contact 76. A second wire or filament 78 extends from the lever 54 in the opposite direction of the first wire 72, around a second pulley 80, and into association with a second electrical contact 82. The wires 72 and 78 (which are commonly referred to as "muscle wires") are formed of a shape memory alloy (e.g., Nitinol), which causes them to heat up and contract when a current flows through them, while being allowed to stretch when the current is removed and the wire 72, 78 cools. Current is alternately applied to the two wires 72 and 78, causing the one carrying a current to heat up and contract while the other one is allowed to stretch. The wire 72, 78 that contacts will pull on the lever 54, causing it to pivot about the pivot point 56. Thus, alternately applying current to the two wires 72 and 78 will cause the wires 72 and 78 to alternately contact and stretch, which in turn causes the lever 54 to pivot back and forth about the pivot point 56.

At the designated time (e.g., 27 hours after the device 10 has been activated), the controller provides commands that cause current to be alternately applied to the muscle wires 72 and 78, which causes the lever 54 to alternately pivot about the pivot point 56 in opposite first and second directions. Pivotal movement of the lever 54 in the first direction will cause the first arm 58 of the lever 54 to engage and rotate the first gear 60 an incremental amount, while pivotal movement of the lever 54 in the second direction will cause the second arm 62 of the lever 54 to engage and rotate the second gear 64 an incremental amount (in the same direction in which the first gear 60 is rotated by the first arm 58). Both gears 60 and 64 are associated with a common shaft 84 (which is shown in FIG. 3 and may be formed with the gears 60 and 64 as a single, molded piece), such that rotation of either gear 60, 64 will cause the shaft 84 to rotate about its central axis. The shaft 84 is mechanically coupled to the piston 28 within the reservoir 14, with rotation of the shaft 84 causing the piston 28 to move toward its initial position (e.g., by a threaded connection whereby rotation of the shaft 84 is translated into movement of the piston 28 along the length of the reservoir 14). As the piston 28 moves toward its initial position (from right to left in the orientation of FIG. 4), it will force the drug out of the reservoir 14 via the proximal end of the needle 38. As described above, the drug will flow through the needle 38, into and through the cannula 34, and into the body of the patient.

After the drug has been delivered (e.g., over the course of a 45-minute session), the controller alerts the patient via a visual cue from the status light 18 and/or an audible cue from the buzzer that drug delivery is complete. Subsequently, the patient removes the device 10 from their skin and discards the device 10.

While devices of the type described above have proven adequate, there is room for improvement of them. For example, there remains a need for an infuser that allows for refilling of the infuser without removing it from the patient.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a drug dispensing system includes a housing containing a drug delivery mechanism and a gas pressure sensor. The housing is configured to receive a replaceable cartridge including a first chamber containing a liquid drug and second chamber having a vacuum pressure or positive gas pressure. The housing also is configured to receive the replaceable cartridge so that the first chamber is in communication with the drug delivery mechanism and the second chamber is in communication with the gas pressure sensor. The gas pressure sensor is configured to detect the gas pressure of the second chamber, and based on the gas pressure detected by the gas pressure sensor the drug dispensing system provides an indication as to whether the replaceable cartridge is suitable for use.

In another aspect, a replacement cartridge includes a first chamber and a second chamber. The first chamber includes a liquid drug and the second chamber includes a vacuum or positive gas pressure. The first chamber is configured to be connected to a drug delivery mechanism and the second chamber is configured to be connected to a pressure sensor of a drug dispensing system.

In yet another aspect, a drug dispensing system including a housing containing a drug delivery mechanism and a photodetector. The housing is configured to receive a replaceable cartridge including a liquid drug. The replacement cartridge is received within the housing such that the photodetector detects light reflected off of the replaceable cartridge. Based on the photodetector's detection of the light reflected off of the replacement cartridge the system provides an indication as to whether the replaceable cartridge is suitable for use.

In another aspect, a replacement cartridge is configured to be inserted into a drug dispensing system so that a surface of cartridge is aligned with a photodetector of the drug dispensing system. The cartridge including a moveable cover that has a first position not covering the surface and a second position covering the surface. The cover in the second position blocks the photodetector from detecting light from the surface, indicating that the cartridge has been previously used and is not suitable for use.

These and other aspects of the present subject matter are set forth in the following detailed description of the accompanying drawings.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

Figure 1:
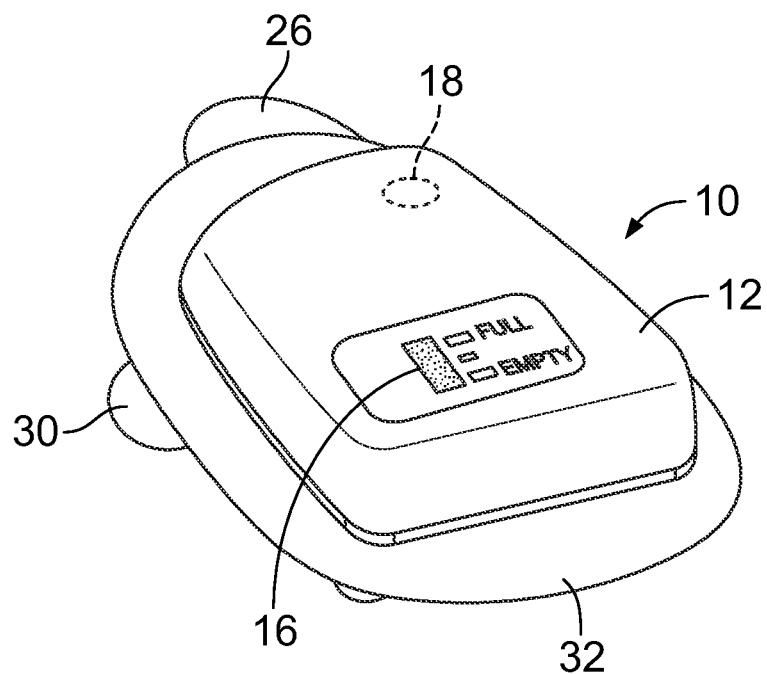
FIG. 1 is a top perspective view of a drug delivery device according to conventional design.
Figure 2:
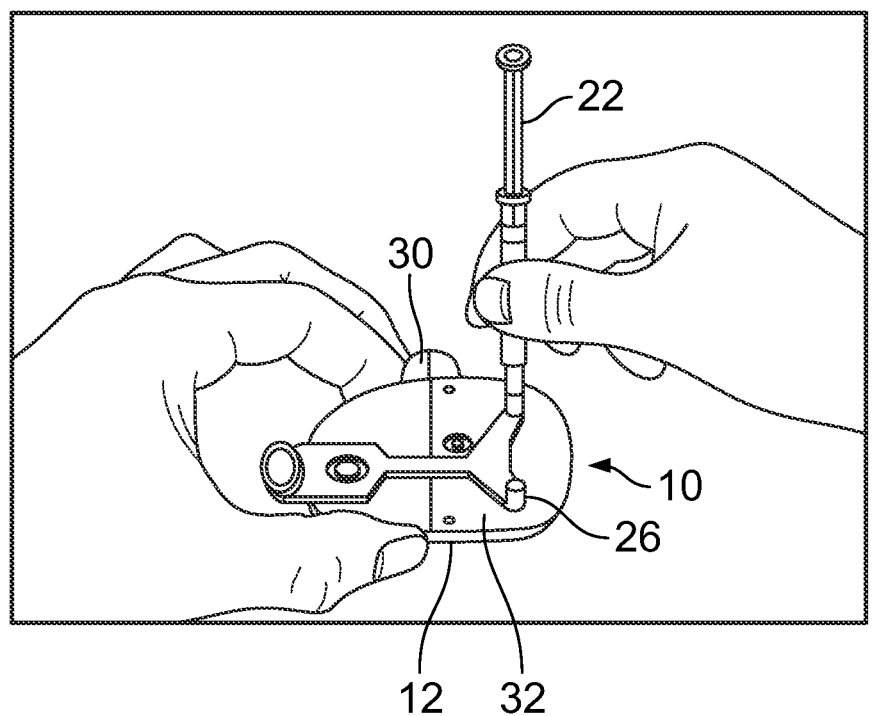
FIG. 2 is a bottom perspective view of the drug delivery device of FIG. 1.
Figure 3:
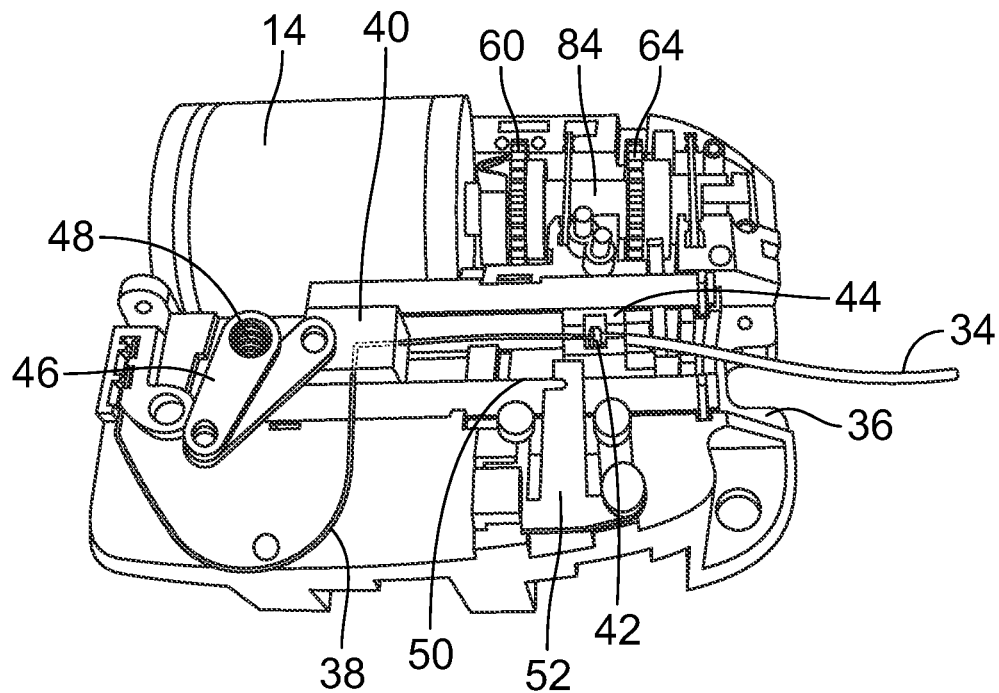
FIG. 3 is a top perspective view of the interior components of the drug delivery device of FIG. 1.
Figure 4:
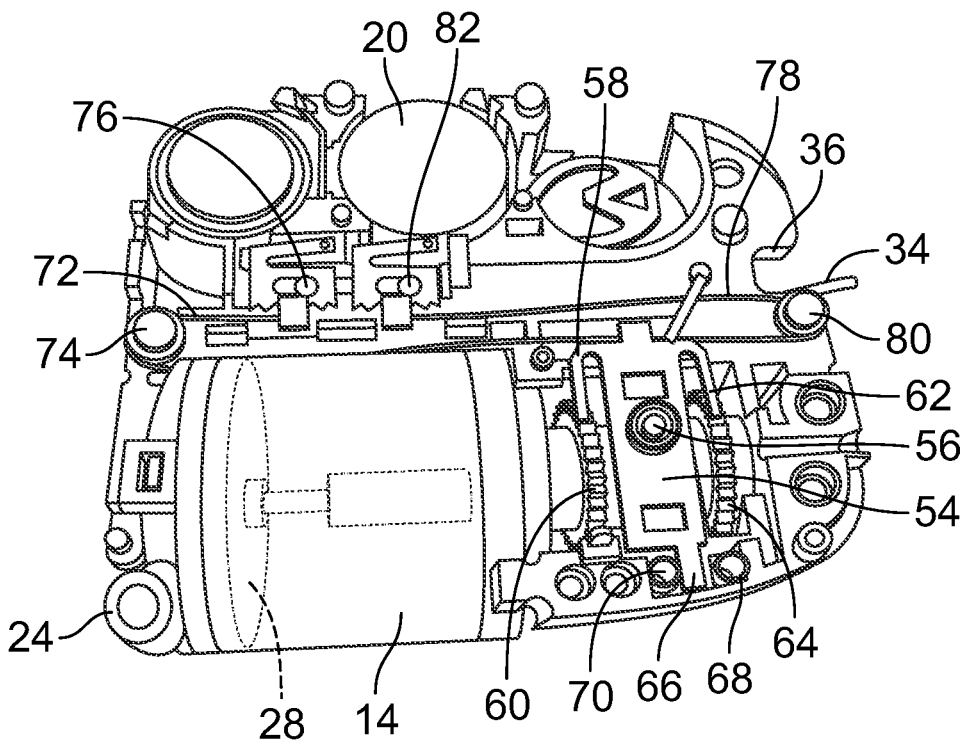
FIG. 4 is a bottom perspective view of the interior components of the drug delivery device of FIG. 1.
Figure 5:
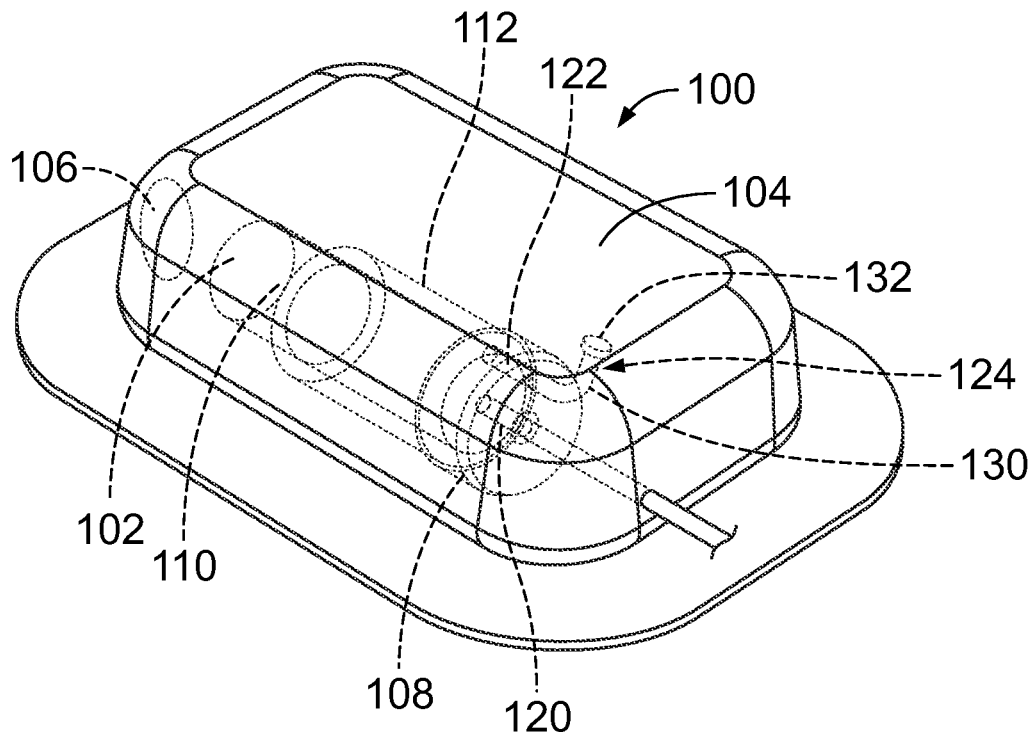
FIG. 5 is a top perspective view of a drug dispensing system of the present disclosure, shown with a replaceable drug supply cartridge received therein.

FIG. 5 illustrates an exemplary embodiment of a drug dispensing system 100 of the present disclosure. The drug dispensing system 100 may be an on-body system or a system carried by the patient. The drug dispensing system 100 employs a replaceable cartridge 102 for supplying and refilling the dispensing system 100 with a liquid drug to be delivered. The methods and systems described herein may be used to deliver any suitable fluid medication to a subject. In an exemplary embodiment, the methods and devices described herein are used to deliver pegfilgrastim to a subject, though other exemplary medications include (without limitation) one or more of the following: adalimumab, rituximab, risankizumab, etanercept, trastuzumab, ado-trastuzumab emtansine, trastuzumab deruxtecan, bevacizumab, infliximab, pegfilgrastim, filgrastim, tocilizumab, golimumab, interferon beta-1a, ranibizumab, denosumab, pembrolizumab, nivolumab, aflibercept, eculizumab, ocrelizumab, pertuzumab, secukinumab, omalizumab, ustekinumab, vedolizumab, daratumumab, dupilumab, atezolizumab, natalizumab, bortezomib, ipilimumab, durvalumab, emicizumab, palivizumab, guselkumab, mepolizumab, panitumumab, ramucirumab, belimumab, abatacept, certolizumab pegol, ixekizumab, romiplostim, benralizumab, evolocumab, canakinumab, obinutuzumab, cetuximab, erenumab, blinatumomab, romosozumab, mirikizumab, inotuzumab, sacituzumab govitecan, enfortumab vedotin, brentuximab vedotin.

During use, the replaceable drug supply cartridge 102, containing a supply of a liquid drug or medicant, is received in a housing 104 of the dispensing system 100 to supply the drug to a drug delivery mechanism (not shown) contained in the housing 104. The housing 104 may be attached to a patient's body and contain any suitable delivery mechanism for delivering the drug to the patient, such as the above-described delivery system. In the illustrated embodiment, the replaceable cartridge 102 is inserted through hole 106 and connected to dock 108. In other embodiments, the replaceable cartridge 102 may be received by housing 104 in any suitable manner, including but not limited to, being docked to the housing 104 or partially inserted into the housing 104. The drug may be, for example, a liquid drug that is delivered from the cartridge 102 by the delivery mechanism into the patient. After the cartridge 102 is empty or spent, the spent cartridge is removed and a new cartridge is docked to the drug dispensing system 100. Thus, the dispensing system may include a plurality of refill cartridges 102.

Figure 6:
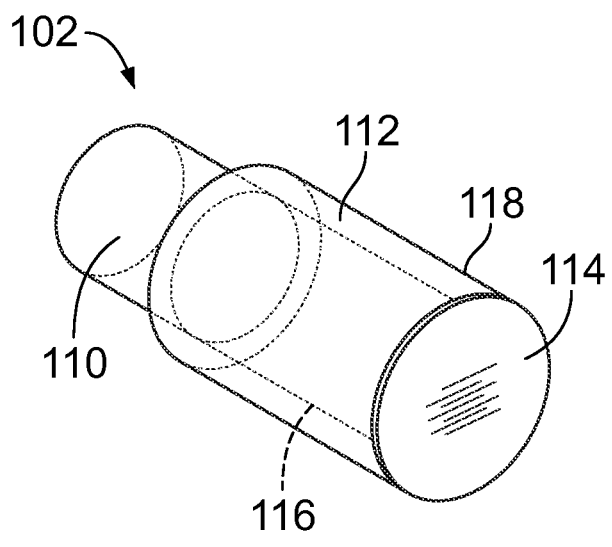
FIG. 6 is a perspective view of one embodiment of a replaceable drug supply cartridge in accordance with the present disclosure.

Referring to FIG. 6, the cartridge 102 includes a first chamber 110 and a second chamber 112. In the illustrated embodiment, the first chamber 110 and the second chamber 112 are coaxial. In other embodiments, the first and second chambers may be in any suitable arrangement, including but not limited to, side-by-side. The first chamber 110 includes the liquid drug therein. For example, the first chamber 110 may be a reservoir of the liquid drug. The second chamber 112 includes a gas pressure that is different from ambient air pressure or the pressure outside of the cartridge 102. The gas pressure of second chamber 112 may be a vacuum or may be a positive pressure. As used herein the term "vacuum" means a gas pressure lower than the air pressure of the environment outside of the cartridge 102, and "positive pressure" means a gas pressure higher than the air pressure of the environment outside of the cartridge 102.

The cartridge 102 also includes at least one breakable or pierceable seal 114 that seals the proximal end 116 of the first chamber 110 and the proximal end 118 of the second chamber 112. In the illustrated embodiment, the at least one seal 114 is a single seal that is circumferentially sealed to the proximal end 116 of the first chamber 110 and circumferentially sealed to the proximal end 118 of the second chamber 112. In other embodiments, the at least one seal 114 may include two or more separate and distinct seals.

Figure 7:
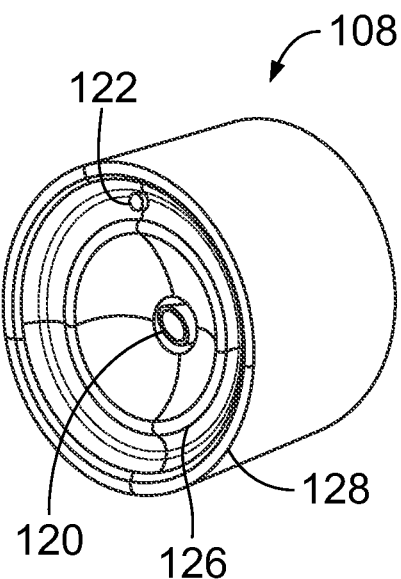
FIG. 7 is a perspective view of one embodiment of a dock of the dispensing system of FIG. 5.

Turning to FIGS. 5 and 7, the dispensing system 100 includes a dock 108 within the housing 104. The dock 108 connects or mates with the cartridge 102. The dock 108 includes a first port 120 that is part of or in communication with the drug delivery mechanism. The dock 108 also includes a second port 122 that is part of or in communication with a gas pressure sensing device 124. The dock 108 further includes an inner sealing surface 126 and an outer sealing surface 128, which contact and form seals 126a and 128a (FIGS. 9 and 10) with the proximal end of the cartridge 102.

Referring to FIGS. 5 and 8-12, the gas pressure sensing device 124 includes duct 130 and a gas pressure sensor 132. The pressure sensor 132 is configured to detect the gas pressure of the second chamber 112 of the cartridge 102. In the illustrated embodiment, the duct 130 is a tube that fluidly connects the port 122 and the gas pressure sensor 132.

Figure 8:
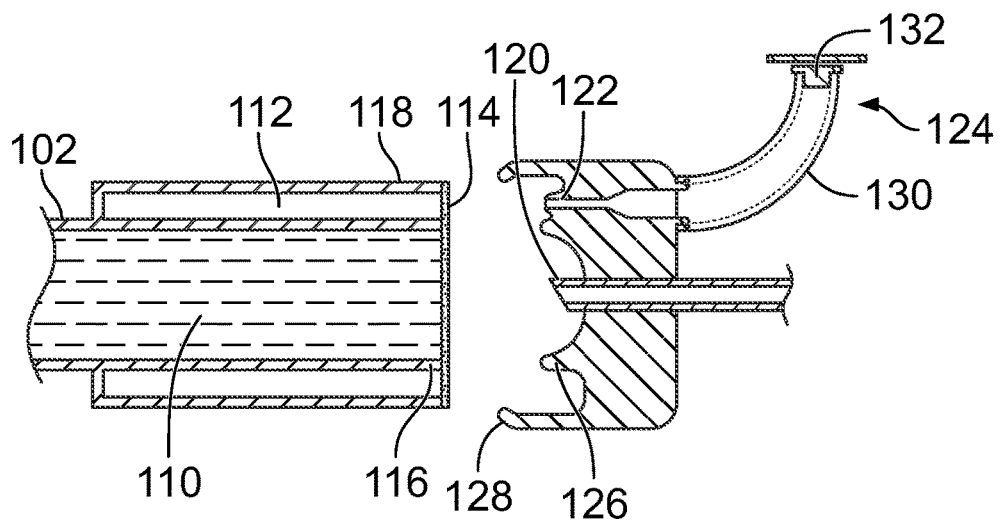
FIG. 8 is a cross-sectional side view of the cartridge of FIG. 6 and dock of FIG. 7 prior to the cartridge being connected to the dock.
Figure 9:
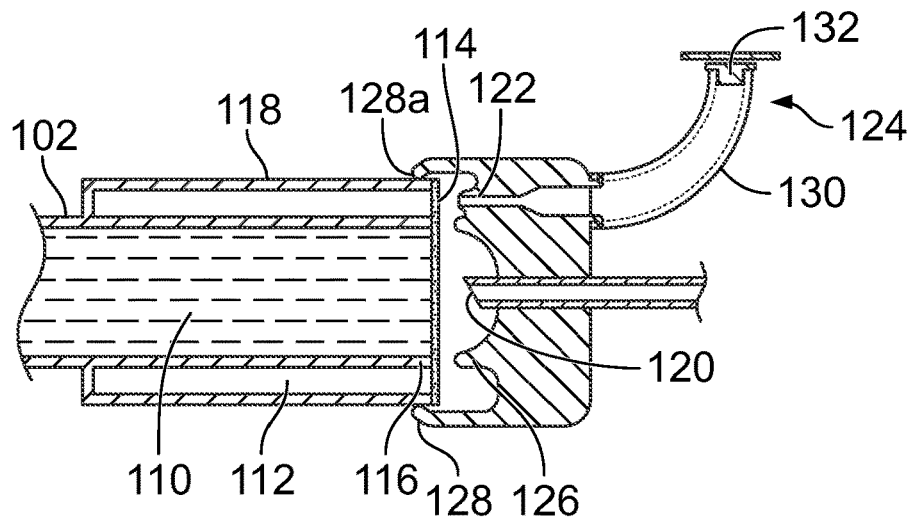
FIG. 9 is a cross-sectional side view of the cartridge of FIG. 6 and dock of FIG. 7 shown with the cartridge contacting an outer seal of the dock.
Figure 10:
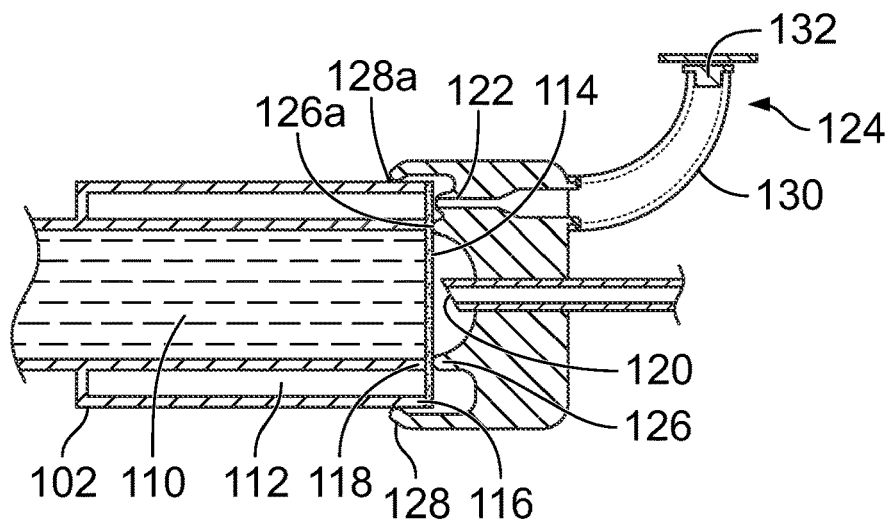
FIG. 10 is a cross-sectional side view of the cartridge of FIG. 6 and dock of FIG. 7 shown with the cartridge contacting an inner seal of the dock.

Turning to FIGS. 8-12, these figures illustrate the replaceable cartridge 102 being received into the housing and being connected to dock 108. Referring to FIG. 8, the cartridge 102 and dock 108 are shown prior to the cartridge 102 being connected to dock 108. Turning to FIG. 9, as the cartridge 102 first contacts dock 108, the outer seal 128 of the dock 108 engages and forms a seal 128a with the proximal end of the cartridge 102, and more particularly in the illustrated embodiment the outer seal engages the proximal end 118 of the second chamber 112. This seal 128a prevents or reduces the effect of ambient air on the pressure of the second chamber 112 when the seal 114 is broken, as described in further detail below. Referring to FIG. 10, as the cartridge 102 moves further into the dock 108, the inner seal 126 contacts the proximal end of the cartridge 102 to form a seal 126a.

Figure 11:
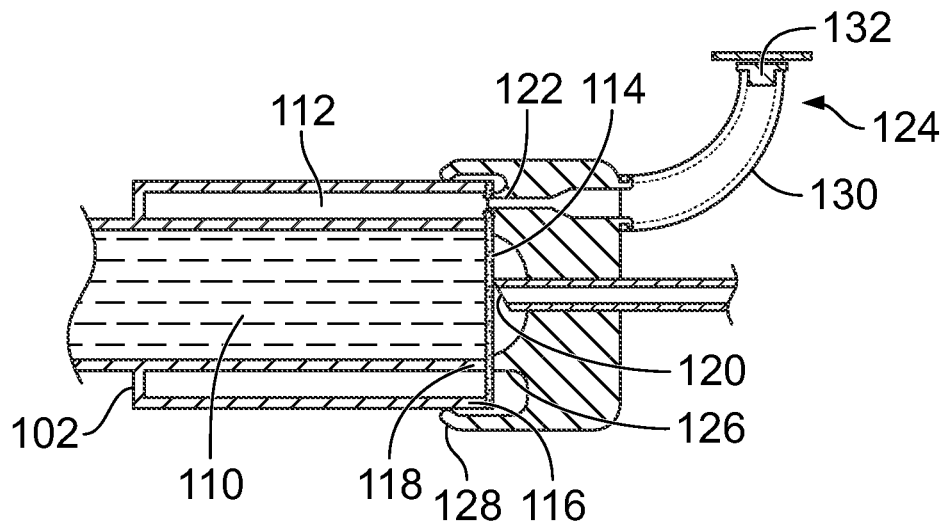
FIG. 11 is a cross-sectional side view of the cartridge of FIG. 6 and dock of FIG. 7 shown with a port of a gas pressure sensing device of the dock in communication with a second chamber of the cartridge.

Turning to FIG. 11, as the cartridge 102 moves further into dock 108, the port 122 pierces seal 114 so that the port 122 is in communication with the second chamber 112. When the port 122 is in communication with the second chamber 112, the pressure sensor 132 is in communication with the second chamber 122 via duct 130 and the pressure sensor 132 detects the gas pressure of the second chamber 122. Based on the gas pressure detected by the gas pressure sensor 132, the system provides an indication as to whether the replaceable cartridge is suitable for use. For example, the system may include an indicator that is in operative communication with the gas pressure sensor 132. The indicator may be a visible indicator, such as a light. In addition to, or in an alternative to, the indication provided by the system 100 may be to allow the drug delivery mechanism to deliver the liquid drug from the first chamber 110. Further, if the gas pressure of the second chamber detected by the gas pressure sensor indicates that the cartridge is not suitable for use, the indication provided by system 100 may be to block the drug delivery mechanism from delivering the liquid from the first chamber 110.

For example, in one embodiment the system 100 is designed so that second chambers 112 of unused cartridges 102 have a vacuum gas pressure. When the cartridge 102 is engaged with dock 108 such that the port 122 is in communication with the second chamber 112, if the pressure sensor 132 detects a vacuum pressure in the second chamber 112, this is an indication that the cartridge 102 is unused, the seal has not been previously broken, or the cartridge is otherwise suitable for use. The system then provides an indication that the cartridge is unused or otherwise suitable for use. On the other hand, if the pressure sensor 132 fails to detect a vacuum pressure in the second chamber 112, this is an indication that the cartridge 102 has been used, the seal has been previously broken, or the cartridge is otherwise suitable for use. The system then provides an indication that the cartridge is not suitable for use.

Alternatively, the system 100 may be designed so that second chambers 112 of unused cartridges 102 have a positive gas pressure. When the cartridge 102 is engaged with dock 108 such that the port 122 is in communication with second chamber 112, if the pressure sensor 132 detects a positive pressure in the second chamber 112, this is an indication that the cartridge 102 is unused, the seal has not been previously broken, or the cartridge is otherwise suitable for use. The system then provides an indication that the cartridge is unused or otherwise suitable for use. On the other hand, if the pressure sensor 132 does not detect a positive pressure in the second chamber 112, this is an indication that the cartridge 102 has been used, the seal has been previously broken, or the cartridge is otherwise suitable for use. The system then provides an indication that the cartridge is not suitable for use.

Figure 12:
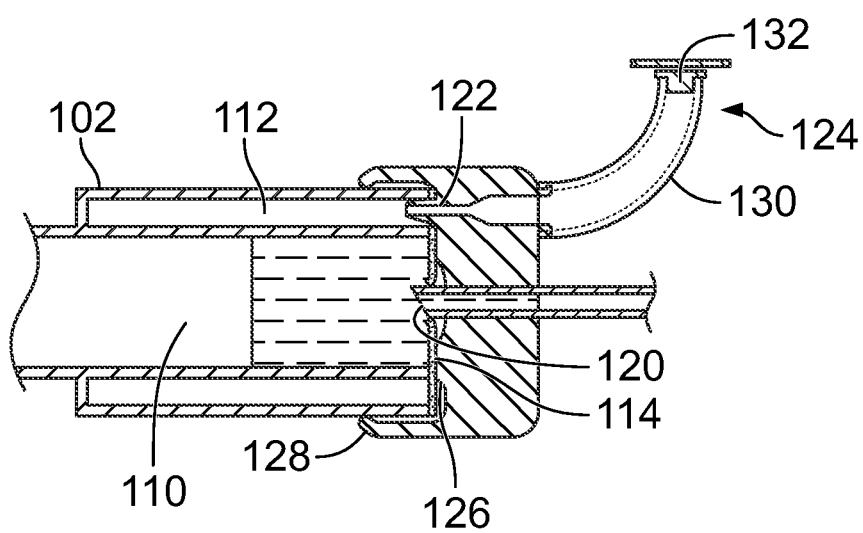
FIG. 12 is a cross-sectional side view of the cartridge of FIG. 6 and dock of FIG. 7 shown with the cartridge fully connected to the dock and a port of a drug delivery mechanism of the dock in communication with a first chamber of the cartridge.

Referring to FIG. 12, the cartridge is moved to fully dock the cartridge 102 with the dock 108. When the cartridge is fully docked, the port 120 pierces the seal 114 and is in communication with the first chamber 110. If the system has indicated that the cartridge is suitable for use, as described above, then the system allows the drug delivery mechanism to deliver the liquid drug from the first chamber 110 to the patient. If, however, the system has indicated that the cartridge is unsuitable for use, the system may provide a warning and/or block delivery of the drug from the first chamber 110.

Figure 13:
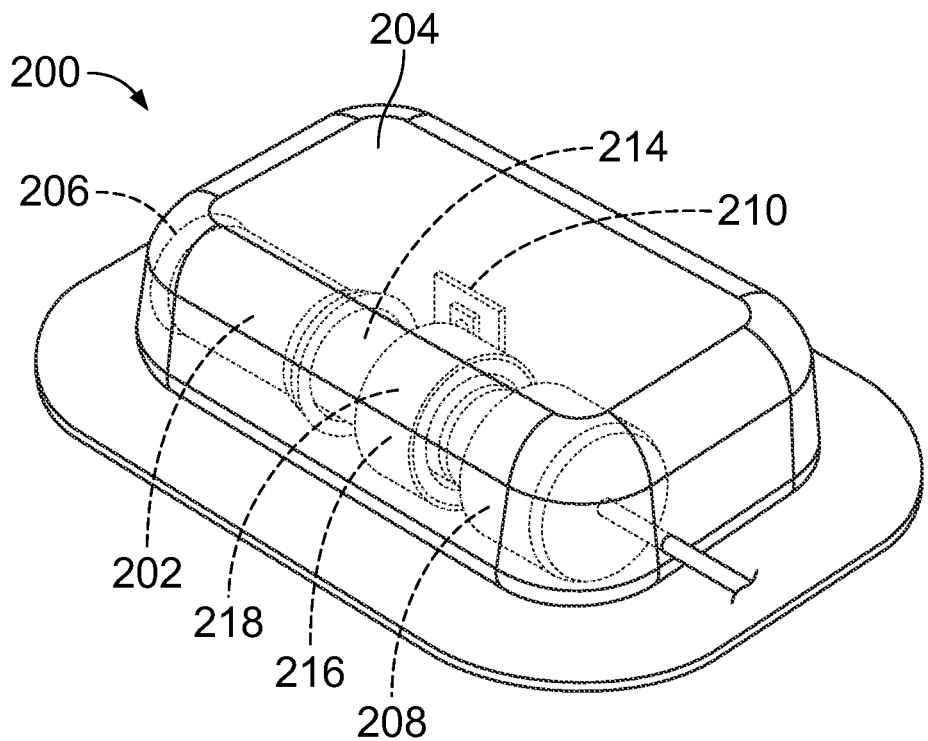
FIG. 13 is a top perspective view of another embodiment of a drug dispensing system of the present disclosure, shown with a replaceable drug supply cartridge received therein.
Figure 14:
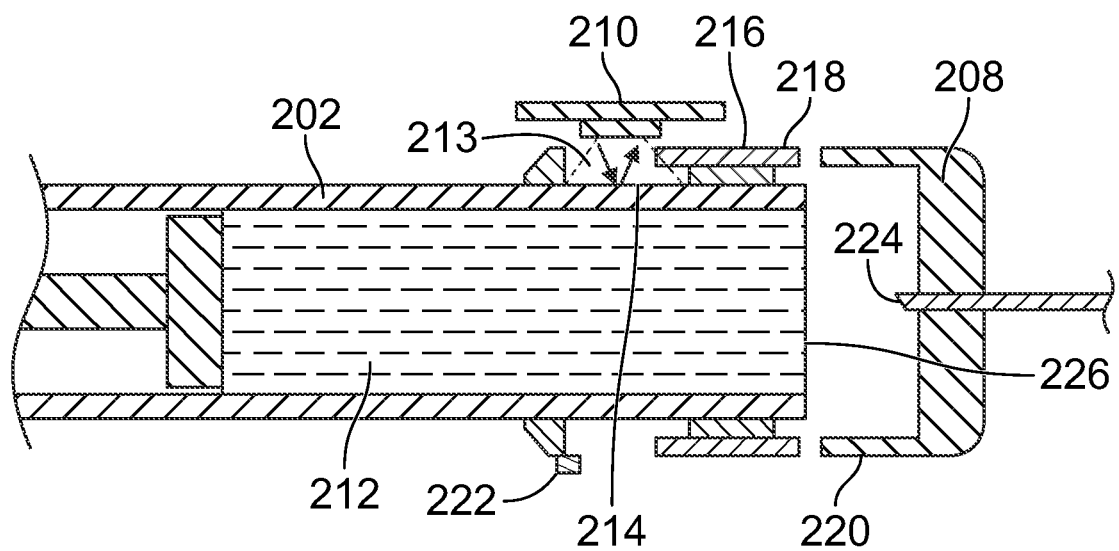
FIG. 14 is a cross-sectional side view of the cartridge and a dock of the drug dispensing system of FIG. 13 prior to the cartridge being connected to the dock.
Figure 15:
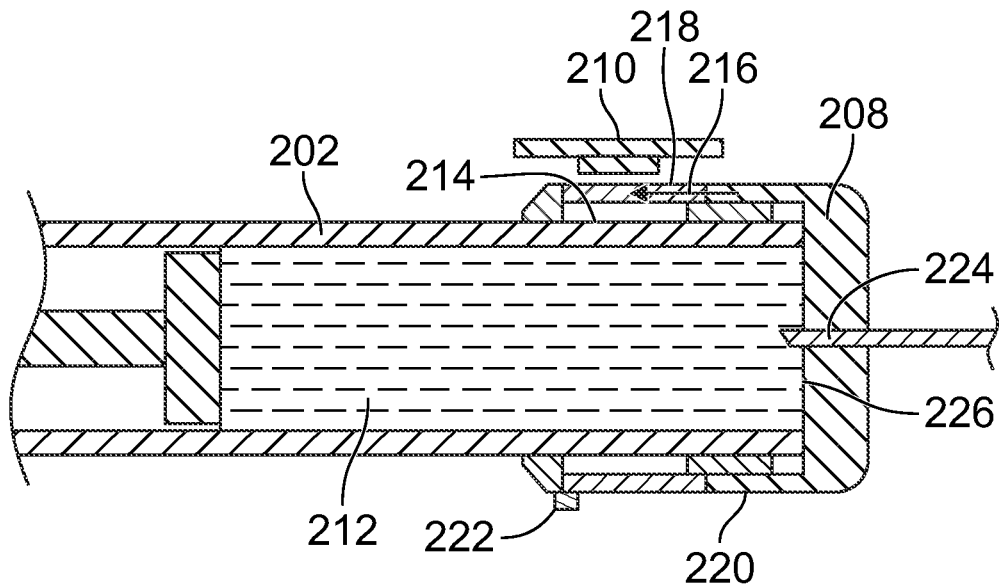
FIG. 15 is a cross-sectional side view of the cartridge and dock of FIG. 14 shown with the cartridge fully connected to the dock and a port of a drug delivery mechanism of the dock in communication with a first chamber of the cartridge.

FIGS. 13-15 illustrate another embodiment of drug dispensing system 200 of the present disclosure. During use, a replaceable drug supply cartridge 202, containing a supply of a liquid drug or medicant, is received in a housing 204 of the dispensing system 200 to supply the drug to a drug delivery mechanism (not shown) contained in the housing 204. The housing 204 may be attached to a patient's body and contain any suitable delivery mechanism for delivering the drug to the patient, such as the above-described dispensing system. In the illustrated embodiment, the replaceable cartridge 202 is inserted through hole 206 and connected to dock 208. The drug may be, for example, a liquid drug that is pumped from the cartridge 202 by the delivery mechanism into the patient. After the cartridge 202 is empty or spent, the spent cartridge is removed and a new cartridge is docked to the drug dispensing system 200. Thus, the dispensing system may include a plurality of refill cartridges 202.

The housing 204 also contains a photodetector 210. The photodetector 210 may be a photoreflector or the photodetector 210 may include a light emitter and a light detector. The housing 204 is configured to receive the replaceable cartridge 202 such that the photodetector 210 detects light 213 (FIG. 14) reflected off of the replaceable cartridge 202. Based on the photodetector's 210 detection of the light reflected off of the replacement cartridge 202 the system provides an indication as to whether the replaceable cartridge is suitable for use. For example, the photodetector's 210 detection of light may indicate that the replaceable cartridge 202 is unused and therefore suitable for use. Alternatively, the photodetector's 210 detection of the reflected light may indicate that the cartridge 202 has previously been used and therefore not suitable for use.

Referring to FIGS. 13-15, the replaceable cartridge 202 includes a chamber 212 including the liquid drug. The replaceable cartridge 202 also includes a surface or section 214 of the cartridge that is aligned with the photodetector 210 when the replacement cartridge 202 is placed into the housing 204. If the photodetector 210 detects light 213 reflected from this surface or segment 214 of the cartridge 202, the system allows the drug delivery mechanism to deliver the drug from replaceable cartridge 202. If the photodetector 210 detects that the light reflected from the surface or segment 214 of the cartridge 202 is obscured, the system does not allow the drug delivery mechanism to deliver the drug from the replacement cartridge. That is, if the photodetector 210 does not detect reflected light, detects partially reflected light, detects light reflecting at a different angle or detects that the reflected light is otherwise obscured, the system does not allow the delivery of the drug and/or provides some other indication.

Figure 16:
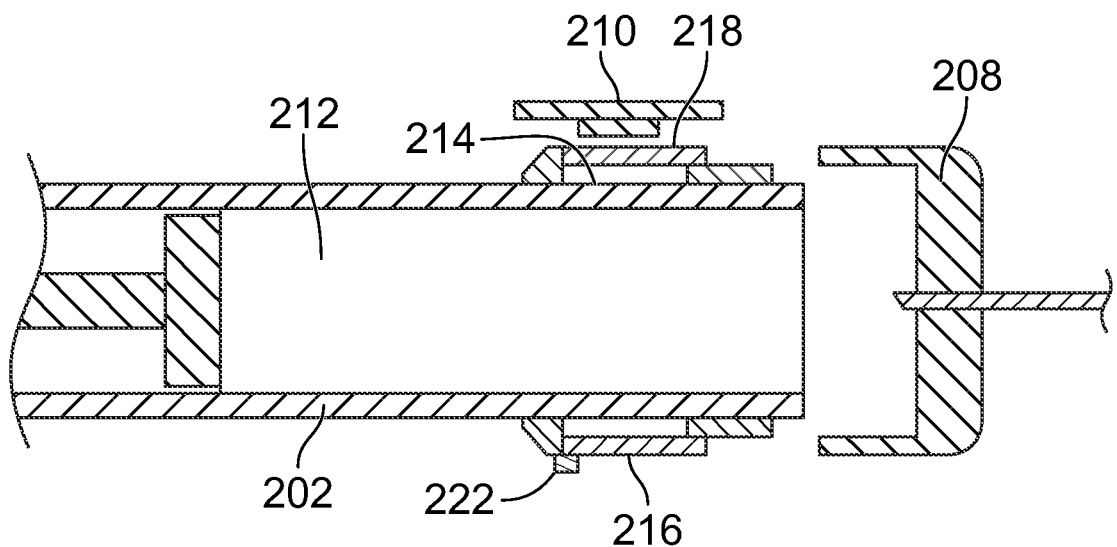
FIG. 16 is a cross-sectional side view of the cartridge and dock of FIG. 14 shown after the cartridge has been removed from the dock.

The replacement cartridge 202 includes a movable cover 216 that is movable from a first position (FIGS. 13 and 14) to a second position (FIGS. 15 and 16). In the first position, the movable cover 216 does not cover the surface or section 214 of the replaceable cartridge 202. In the second position the cover 216 obscures the surface or section 214. For example, the cover at least partially blocks, blocks and/or alters the reflection of light from the surface or section 214. In the illustrated embodiment the cover 216 is a movable collar coaxially positioned about the cartridge 202. Furthermore, the surface 218 of the cover 216 may be selected to have a different light reflection property than the surface 214 of the cartridge 202. For example, the surface 218 of the cover 216 may be rougher or less reflective than the surface 214. In an alternative, the surface 218 of the cover 216 may be more reflective, but angled to direct the light away from the detector.

Referring to FIGS. 13 and 14, when the cartridge 202 is unused, the cover 216 is located in the first position. The cartridge 202 is inserted into the housing 204 and the detector 210 detects light 213 reflected from the surface or section 214 of the cartridge 202. When the detector 210 detects light 213 reflected from this surface 214, this is an indication that the cartridge 202 is unused and suitable for use. Turning to FIG. 15, when the cartridge 202 is connected to dock 208, the outer wall 220 of the dock 208 engages the cover 216, and as the cartridge 202 is pushed into the dock 208, the cover 216 and cartridge 202 move relative to each other such that the cover 216 moves into the second position and obscures the surface 214 of the cartridge 202. In the illustrated embodiment, the cover 216 at least partially covers the surface 214 to obscure the surface. Optionally, the cover 216 is locked into the second position by a lock 222. Furthermore, a port 224 of the dock 208 pierces a seal 226 of the cartridge 202 so that the chamber 212 containing the liquid drug is in communication with the port 224. The port 224 is in communication with drug delivery mechanism. Optionally, when an unused cartridge 202 is inserted into the housing the detector's 210 detection of light 213 reflected by the surface 214 and then detection of light reflected by the cover 216 may be an indication that the cartridge 202 has been fully docked to the dock 208.

When the used or spent cartridge 202 is removed from the housing 204 the cover 216 remains in the second position covering the surface 214. In an alternative embodiment, the cover 216 is not moved into the second position until the cartridge 202 is removed from the housing 204. That is, upon removal from the housing 204, the cover 216 is moved into the second position. Referring to FIG. 16, if the cover 216 blocks the detector 210 from detecting light reflected off of the section 214, and/or detects light reflected off of the cover 216, this is an indication that cartridge 202 is unsuitable for use because it has already been used or is spent. The system provides such an indication and/or prevents liquid drugs from being delivered from the cartridge 202.

Figure 17:
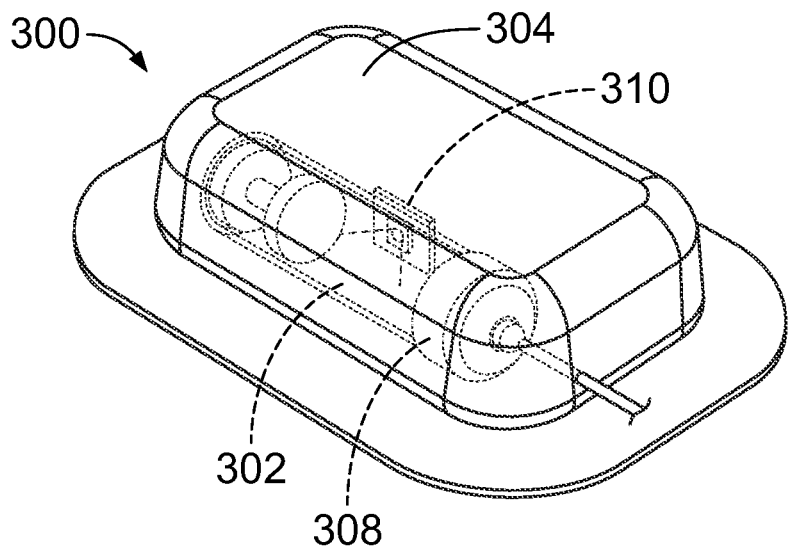
FIG. 17 is a top perspective view of another embodiment of a drug dispensing system of the present disclosure, shown with a replaceable drug supply cartridge received therein.
Figure 18:
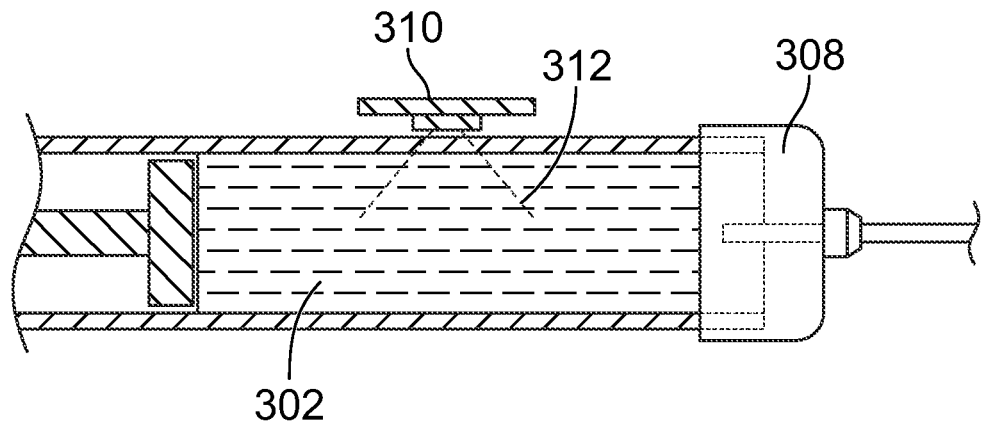
FIG. 18 is a cross-sectional side view of the cartridge, a dock and a photodetector of FIG. 17 shown with the cartridge fully connected to the dock and a port of a drug delivery mechanism of the dock in communication with a first chamber of the cartridge.
Figure 19:
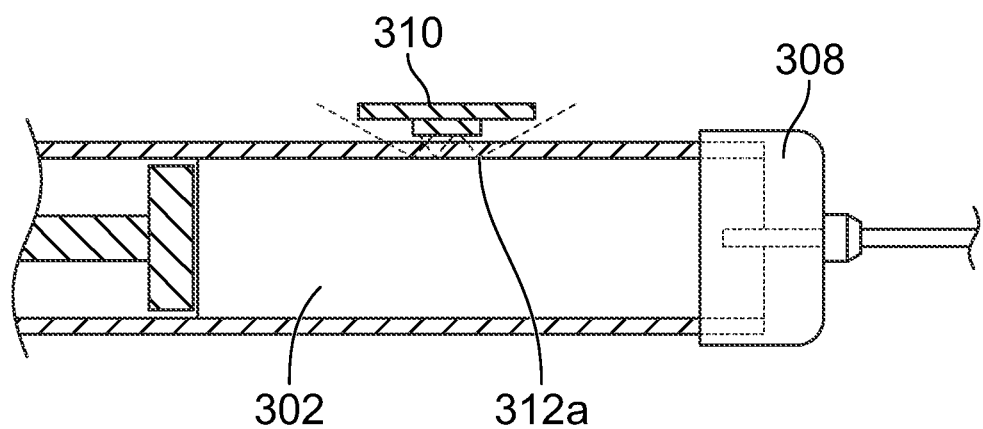
FIG. 19 is a cross-sectional side view of the cartridge, dock and photodetector of FIG. 17 shown after the first chamber has been emptied.

FIGS. 17-19 illustrate another embodiment of a drug dispensing system 300 of the present disclosure. In this embodiment, a photodetector 310 is used to detect whether a cartridge 302 is full of the liquid drug or is empty. The cartridge 302 is made of a transparent material. Comparing FIGS. 18 and 19, when the cartridge 302 is substantially filled with a liquid drug, the difference in indices of refraction is small between the transparent material (plastic or glass) of the cartridge 302 and the liquid within the cartridge 302. Therefore, a relatively large amount of light 312 passes through the cartridge 302 and liquid (FIG. 18) and a relatively small amount of light is reflected back at the photodetector 310. On the other hand, when the cartridge 302 is empty or at least not full, the difference in indices of refraction is large between the translucent material (plastic or glass) of the cartridge 302 and the air within the cartridge. Therefore, a relatively large amount of light 312a is reflected off of the cartridge 302 (FIG. 19).

Accordingly, when a cartridge 302 is inserted into the housing 304 and docked with the dock 308, if the photodetector 310 detects the relatively small reflection of light 312, this is an indication of that the cartridge 302 is full and suitable for use. The system provides an indication of the cartridge being suitable for use and allows the drug delivery mechanism to dispense the liquid drug from the cartridge 302. However, if the photodetector 310 detects the relatively large reflection of light 312a off of the cartridge 302, this is an indication that the cartridge 302 has been already used or spent and is not suitable for use. The system then provides an indication of the cartridge being unsuitable for use. While an empty or at least not full cartridge 302 reflects a greater amount of light in the illustrated embodiment, it should be understood that it is within the scope of the present disclosure for a smaller amount of light to instead be reflected to indicate prior use of the cartridge 302.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A drug dispensing system, comprising:
   a housing containing a drug delivery mechanism and a photodetector;
   a plurality of replaceable cartridges containing a liquid drug;
   one of the replaceable cartridges being received within the housing such that the photodetector detects light reflected off of the one replaceable cartridge, wherein based on the photodetector's detection of the light reflected off of the one replaceable cartridge the drug dispensing system provides an indication as to whether the one replaceable cartridge is suitable for use;
   wherein when the one replaceable cartridge is received within the housing and the photodetector detects light reflected off of the one replaceable cartridge, the drug dispensing system allows the drug delivery mechanism to deliver the liquid drug from the one replaceable cartridge; and
   when the one replaceable cartridges is received within the housing and the photodetector does not detect light reflected of off the one replaceable cartridge, the drug dispensing system provides an indication that the one replaceable cartridge is not suitable for use.

2. The system of claim 1, wherein the photodetector is a photoreflector.

3. The system of claim 1, wherein the photodetector comprises a light emitter and a light detector.

4. The system of claim 1, wherein when the replaceable cartridge is received within the housing and the photodetector detects light reflected from said surface, the drug dispensing system allows the drug delivery mechanism to deliver the liquid drug from the replaceable cartridge.

5. A drug dispensing system,
   a housing containing a drug delivery mechanism and a photodetector;
   the housing configured to receive a replaceable cartridge including a liquid drug, the replaceable cartridge received within the housing such that the photodetector detects light reflected off of a surface of the replaceable cartridge, wherein when the photodetector detects light reflected from said surface of the replaceable cartridge, the drug dispensing system allows the drug delivery mechanism to deliver the liquid drug from the replaceable cartridge; and
   wherein the replaceable cartridge further includes a moveable cover that is moveable from a first position not covering said surface to a second position wherein the cover obscures said surface;
   the cover being in the first position prior to use of the replaceable cartridge so that the light reflected from said surface is detectable by the photodetector; and
   the cover being in the second position after use of the replaceable cartridge such that the cover obscures said surface and light reflected from the surface is obscured from the photodetector.

6. The system of claim 5, wherein when the cover is moved to the second position, the cover becomes locked in the second position.

7. The system of claim 5, wherein the replaceable cartridge comprises a chamber containing the liquid drug, and the cover comprises a slidable collar positioned about the chamber.

8. The system of claim 5, further including a dock associated with the housing, wherein the cover is configured to be moved into the second position upon connecting the replaceable cartridge to the dock.

9. The system of claim 5, wherein the cover is configured to be moved into the second position upon removing the replaceable cartridge from the housing.

10. The system of claim 5, wherein the photodetector is a photoreflector.

11. The system of claim 5, wherein the photodetector comprises a light emitter and a light detector.

12. A drug dispensing system, comprising:
    a housing containing a drug delivery mechanism and a photodetector;
    the housing configured to receive a replaceable cartridge including a liquid drug, the replaceable cartridge received within the housing such that the photodetector detects light reflected off of the replaceable cartridge, wherein based on the photodetector's detection of the light reflected off of the replaceable cartridge the drug dispensing system provides an indication as to whether the replaceable cartridge is suitable for use;
    wherein the replaceable cartridge includes a chamber containing the liquid drug and defined by a chamber wall, and the chamber wall reflects a first amount of light when the chamber is substantially filled with the liquid drug prior to use and reflects a different second amount of light when the chamber has a lesser amount of the liquid drug after use has commenced; and
    when the replaceable cartridge is received within the housing and the photodetector detects the first amount of light reflected from said chamber wall, the drug dispensing system allows the drug delivery mechanism to deliver the liquid drug from the replaceable cartridge; and
    wherein when the replaceable cartridge is received within the housing and the photodetector does not detect the first amount of light reflected from the chamber wall, the drug dispensing system provides an indication that the replaceable cartridge is not suitable for use.

13. The system of claim 12, wherein the chamber wall is at least partially transparent.

14. The system of claim 12, further including a dock within the housing.

15. The system of claim 12, wherein the photodetector is a photoreflector.

16. The system of claim 12, wherein the photodetector comprises a light emitter and a light detector.

17. A drug dispensing system, comprising:
- a housing containing a drug delivery mechanism and a photodetector, the photodetector comprising a light emitter and a light detector;
- a plurality of replaceable cartridges containing a liquid drug; and
- one of the replaceable cartridges being received within the housing such that the photodetector detects light reflected off of the one replaceable cartridge, wherein based on the photodetector's detection of the light reflected off of the one replaceable cartridge the drug dispensing system provides an indication as to whether the one replaceable cartridge is suitable for use.

18. The system of claim 15, wherein the photodetector is a photoreflector.

19. The system of claim 17, wherein the photodetector comprises a light emitter and a light detector.

* * * * *